United States Patent [19]
Chatterton

[11] 3,979,326
[45] Sept. 7, 1976

[54] DRY FOAM PRODUCING APPARATUS

[76] Inventor: James Chatterton, 2916 Philadelphia Drive, Dayton, Ohio 45405

[22] Filed: Apr. 11, 1974

[21] Appl. No.: 459,882

[52] U.S. Cl. .............................. 252/359 E; 239/343; 261/DIG. 26; 259/DIG. 36; 169/14
[51] Int. Cl.² ..................... B01J 13/00; A62C 35/00
[58] Field of Search ............... 252/359 E, 361, 321; 159/DIG. 4; 202/264; 203/20; 195/107; 259/DIG. 36; 239/343; 55/221; 261/DIG. 26; 169/14

[56] References Cited
UNITED STATES PATENTS

| | | | |
|---|---|---|---|
| 1,753,429 | 4/1930 | Rice | 252/359 E UX |
| 2,335,339 | 11/1943 | Keen | 252/359 E X |
| 2,386,464 | 10/1945 | Hogenmiller | 261/DIG. 26 |
| 2,512,456 | 6/1950 | Boyd et al. | 252/359 E UX |
| 2,524,421 | 10/1950 | Boerner et al. | 261/DIG. 26 |
| 2,577,025 | 12/1951 | Lundberg | 252/359 E UX |
| 2,715,045 | 8/1955 | Thompson | 252/359 E UX |
| 3,118,958 | 1/1964 | White | 252/359 E |
| 3,711,070 | 6/1973 | Khokhlov | 159/DIG. 4 |

FOREIGN PATENTS OR APPLICATIONS

| | | | |
|---|---|---|---|
| 1,045,049 | 11/1953 | France | 252/359 E |
| 54,162 | 2/1943 | Netherlands | 261/DIG. 26 |

Primary Examiner—Jack Sofer
Attorney, Agent, or Firm—Jerome P. Bloom

[57] ABSTRACT

Foam producing apparatus comprising a container adapted to receive a small amount of chemical solution in its bottom including means for converting said solution into an extremely large volume of relatively "dry" foam. In connection with the container are series related means uniquely formed and arranged to wring and extract liquid from the bubbles of the foam at successive intervals in the course of its flow.

Preferred applications of the invention contemplate the use of the "dry" bubbles of the foam as a vehicle for various chemicals such as weed killers, insecticides and fertilizers which will have the capability of an adherent deposit of the chemicals without significant dilution of their required strength.

14 Claims, 4 Drawing Figures

U.S. Patent   Sept. 7, 1976   3,979,326
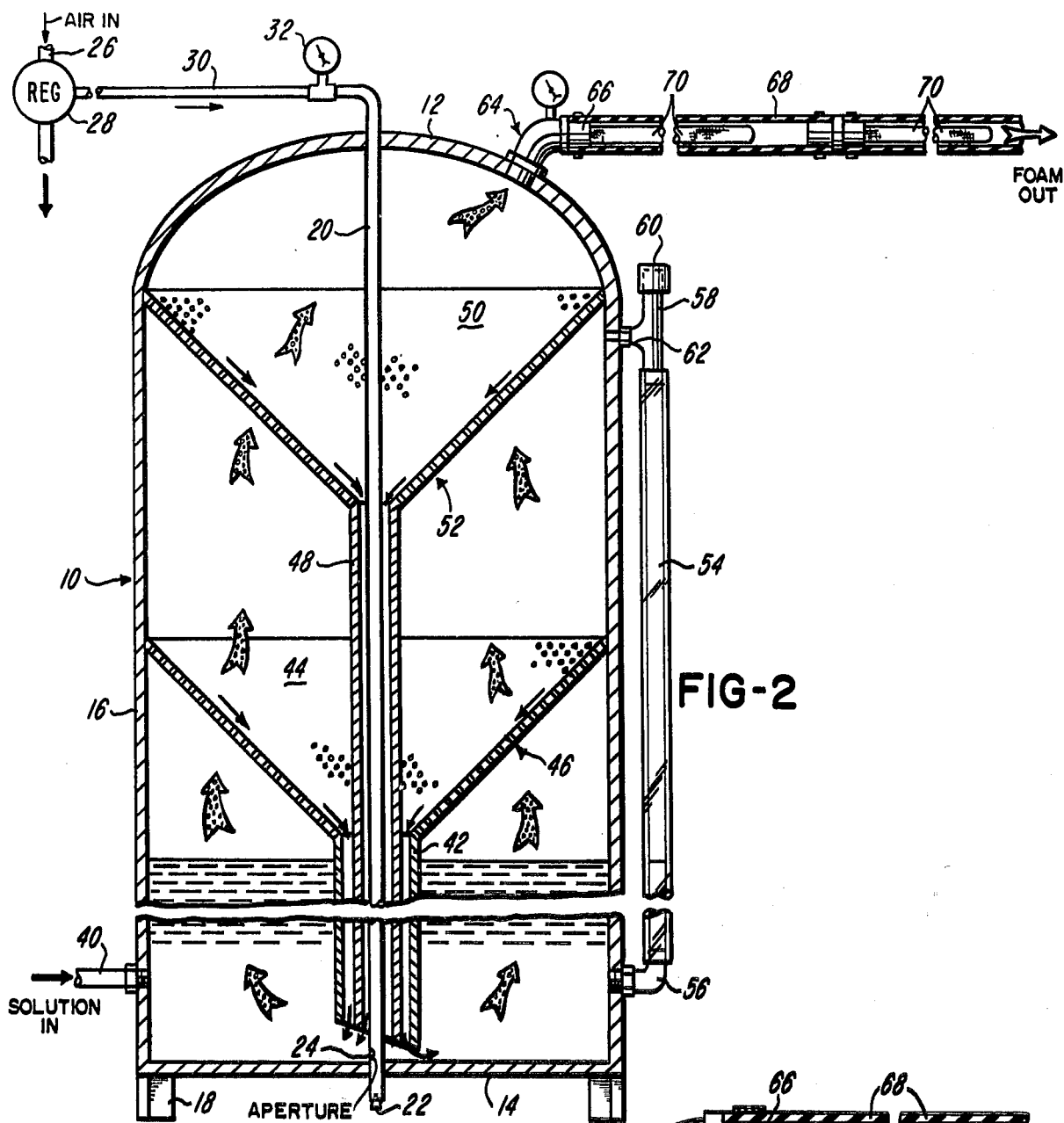
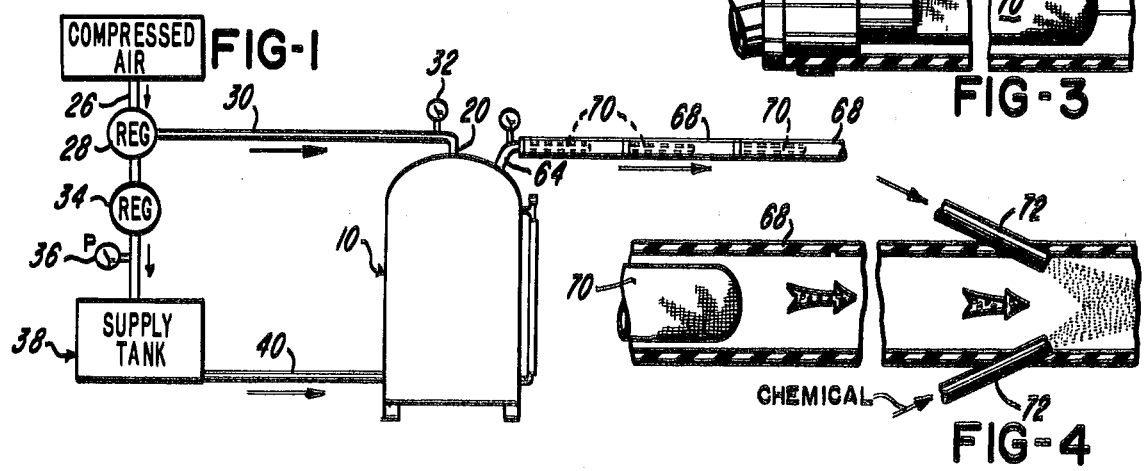

DRY FOAM PRODUCING APPARATUS

BACKGROUND OF THE INVENTION

This invention relates to improvements in foam producing equipment. Embodiments have a wide field of application and particular utility for use in spreading fertilizer and weed killer and will be so described. However, its application is not so limited and such is not intended. It has obvious use, of course, in fighting fire, as well as serving as an excellent vehicle for cleansing materials.

Agriculture has long needed a better and more effective way of spreading fertilizer and weed killer. All types of spreading equipment have been developed and applied to such purposes but difficulties still remain. The means used for and the manner of application generally leave the fertilizer or weed killer materials at the mercy of the elements. If the materials are applied in a dry form, then the winds tend to dissipate and cause a non-uniform and inadequate distribution. If applied in wet form the materials are more difficult to control and the active materials often times prove to be more dilute than required for the environment of their application or too concentrated, in either case giving poor results. The optimal condition of their application is in a relatively dry form provided they can be made to adhere to the place of their original deposit. Only in this way can the strength of the fertilizer or weed killer application be insured and its most effective and economical use obtain.

SUMMARY OF THE INVENTION

The present invention provides apparatus for producing an unusually dry foam in which active materials such as fertilizer, weed killer, fire damping chemicals or cleansing chemicals may be embodied or to which they may attach for most effective application to their required use.

In preferred embodiments the invention provides a foam producing container receiving in its bottom a small amount of liquid, preferably a solution of water and detergent, to which a metered flow of air is applied under controlled pressure to cause the solution to be gradually converted into globe or bubble form. These globes or bubbles rise above the liquid level in the container to pass through apertures in vertically spaced structures by means of which they are successively squeezed, have a portion of their water content extracted, and caused to successively reform. The extracted water is caused to drain back to replenish the liquid content in the bottom of the container.

In sophisticated systems demanding a continuing production of foam, a source of supply of the liquid solution is connected with the bottom of said container and means are provided for a controlled delivery thereof to maintain the liquid level desired in the container.

In any event the globes or bubbles are formed and reformed and as the air under pressure continues to move to and through the liquid solution, the foam of bubble form so produced eventually and quickly fills the container and is forced through a restricted opening at its top which causes a further squeezing of the bubbles as they move in a foam condition to a delivery hose. In the introduction of the foam to and passage thereof through the hose, the foam will pass through one or more sacks of porous fiber which further extracts water from the wall forming each bubble. The net result is that the foam delivered from a small amount of solution has a great volume but is relatively quite dry. The condition thereof is such that if any active agents are embodied in the original solution they have substantially full exposure to the surface on which the bubbles of the foam produced are deposited. There is nevertheless enough liquid to cause the bubbles to adhere to where they are deposited.

The invention thus provides a means where active fertilizer or weed killer may be mixed into a basic solution and carried out therefrom embodied in an extremely dry foam vehicle.

An alternative provided by the invention is to inject the fertilizer, weed killer, or active agent of any other sort, into the form per se to be carried in or on the surfaces of its bubble content to the place of deposit.

A primary object of the invention is to provide improved means for spreading and depositing fertilizer weed killer or other surface active agents.

Another object of the invention is to provide improved foam producing apparatus which is economical to fabricate and employ, more efficient and satisfactory in use, adaptable to a wide variety of applications and unlikely to malfunction.

A further object of the invention is to provide means for producing an extremely dry foam serving as an excellent vehicle for spreading agricultural chemicals, firefighting chemicals, cleansing chemicals and the like.

An additional object of the invention is to provide foam producing apparatus and means for and methods of its use possessing the advantageous features and the inherent meritorious characteristics herein described.

With the above and other incidental objects in view as will more fully appear in the specification, the invention intended to be protected by Letters Patent consists of the features of construction, the parts and combinations thereof, and the mode of operation as hereinafter described or illustrated in the accompanying drawings, or their equivalents.

Referring to the drawings wherein some but not necessarily the only forms of embodiment of the invention are illustrated, FIG. 1 is a schematic illustration of a system embodying the foam producing apparatus of the invention;

FIG. 2 is a sectional view of said foam producing apparatus taken in vertical elevation;

FIG. 3 is an enlarged view of a foaming device in the delivery line of said foam producing apparatus; and FIG. 4 illustrates a modification of the foam producing apparatus of the invention illustrating a method of utilizing the surface of the foam composition as a vehicle for the spreading of active chemicals.

Like parts are indicated by similar characters of reference throughout the several views.

A preferred embodiment of the foam producing concept of the invention is illustrated in FIG. 2 as embodied in a container 10 which has a dome shaped top 12 a base 14 and a peripheral wall 16. The base 14 is elevated from a supporting surface by block like projections 18. Projecting through the container 10 and positioning vertically thereof, about its central axis, is a small bore air delivery tube 20. One end of the tube 20 projects through an aperture in the base 14, a seal bing provided thereabout. The extremity of the tube which is below the base 14 is sealed by a plug 22, the removal of which will facilitate a cleaning of the tube, as and when required. Within the container 10 and immediately above its base 14 the tube 20 is provided with one or more apertures 24 the purpose of which will soon be obvious. The end of the tube 20 which projects through the dome 12 at the top of the container is coupled to a source of compressed air under pressure. An air delivery line 26 extending from the source has incorporated therein a pressure regulator 28 and a branch line 30 affords a conduit leading from the regulator 28 which is coupled to the inlet end of the tube 20. A pressure gage 32 is incorporated in the branch line 30.

Beyond the regulator 28, the line 26 is extended and incorporates a second regulator 34 and in following relation thereto a pressure gage 36. The end of the delivery line 26 beyond the gage 36 is projected through the top of a tank 38, a seal being provided about the line 26 where it passes through the wall of the tank 38. The tank 38 serves as a container for a supply of a detergent solution which is used in producing foam per the present invention. A supply line 40 extends from the bottom of the tank 38 and connects into the peripheral wall 16 of the container 10, adjacent its lower end, a seal being provided thereabout at the point of its connection.

The source of the compressed air may be provided by any conventional and suitable means which may for example provide a supply of air under a pressure of 200 psig. In the practice of the invention the pressure regulators, which also may be of conventional nature, may be so set and controlled that for example the air delivered to and through line 30 to tube 20 will be under pressure of 30 psig while the air delivered to the tank 38 and applied to the top level of the solution therein may be maintained at a level somewhat in excess of 6 psig. The system has been and can be arranged, with suitable and conventional controls, that 10% or less of the volume of the container 10, at its lower end, is maintained filled with a detergent solution suitable for foaming purposes to suit the intended application. To this solution may be added the active chemical agent or agents, such as fertilizers that are intended to be delivered and spread in a foam vehicle per the present invention.

The particular detail of the plumbing, the gages, the regulators and other controls which may be embodied in the system are not shown or described in any detail since in and of themselves such details are not required for an understanding of the present invention and can be variously chosen and applied from available sources of such material by a mechanic versed in the art.

Within the container 10, vertically spaced from each other and the level of the solution in the bottom of the container are two funnel shaped devices 46 and 52. The uppermost device 52 is in the shape of a conical bowl 50 which has a plurality of uniform and small apertures affording passages through the wall thereof. The base of the conical shape of the bowl defined at the mouth thereof is uppermost and defines a plane coincident with that forming the base of the dome 12 of the container 10. The apex of bowl 50 is lowermost and has a central aperture about which a tube 48 depends from the bowl, about and in closely spaced concentric relation to the air delivery tube 20. The lower end of tube 48 terminates adjacent but spaced above the aperture or apertures 24 in the tube 20. The lowermost device 46 includes an apertured bowl 44 identical in shape and size to the bowl 50 except that the aperture at its dependent apex is sufficiently large to permit free passage of the tube 48 as it depends about the tube 20. In connected relation to and dependent from the bowl 44 about the aperture in its apex is a tube segment 42 the lower end of which is cut on the bias and terminates also above the apertures 24 so as to provide clear passage of air therefrom into the solution at the bottom of the container 10. Preferably both the tubes 42 and 48, which are in concentric closely spaced relation, have their lower ends cut on a bias to occupy a common plane as shown in FIG. 2.

Connected at one side of the container 10 is a clear plastic tube 54 constituting a sight gage for observing the level of liquid in the container 10. The lower end of tube 54 is mounted to provide a vertical extension of one end of elbow type coupling 56 the other end of which is threadedly engaged into the side of the container 10 adjacent its base. A tubular adapter 58 which forms a vertical extension of tube 54 has a cap 60 and a tubular branch 62 at one side by means of which the tube 54 is communicated with the interior of the container 10 at its upper end, for reasons which will be obvious and to permit the sight gage to function. Also on removal of the cap 60, it permits the introduction of solution to the container 10 by way of tube 54, if needs require.

An elbow-type coupling device 64 is threadedly engaged in the dome 12 of the container 10 to serve as a discharge outlet for foam produced therein. An adapter 66 forming an extension of the elbow device 64 provides a reduction in external diameter to enable the coupling thereto by suitable means, of one end of a section of a delivery hose 68. Within the hose 68 the adapter 66 has a tubular extension further reduced in external diameter over which is clamped one end of a sock-like extension 70 woven porous cloth the body of which is tubular and has a diameter less than that of the hose 68 and terminates in a closed end remote from the open end coupled to the adapter 66.

In function of the apparatus of the invention the operation is started with a limited amount of detergent solution the bottom container 10, the solution being dependent on the application and, for example, embodying a fertilizer composition. On delivery of air through the tube 20, under pressure at a level of 10 to 50 psig, depending on the application, the air moves, by way of aperture or apertures 24 into the interior of the detergent solution in the bottom of the chamber defined by container 10. The compressed air inherently agitates the liquid, forming bubbles, the liquid encapsulating pockets of air. The bubbles or globes so formed rise in a layered effect, piling up over the liquid. As the bubbles reach the bowl 44, which bridges a central section of the vertical extent of the container, they are forced therethrough. The apertures in the bowl 44, which may be 3/32 inches, for example, provide a squeezing of the bubbles as they pass therethrough and reform above the bowl 44. The result is an extraction of some of the water content of the wall of solution forming each bubble, which extracted liquid will adhere to and move down the bowl surface and drain back to the liquid level of the solution in the bottom of the container along the surface of tube segment 42. As the bubbles rise and create further layers of foam in the container 10, they reach the bowl 50 which bridges the upper end of the container wall 16. At this point the bubbles of the foam are squeezed through the small apertures in bowl 50 in the process of which a further amount of water is squeezed therefrom to drain back to the liquid level in the bottom of the container along tube 48. The bubbles of the foam reform above the bowl 50 in a state wherein the water content of the wall thereof has been diminished and the foam at this level becomes "drier".

As the foam bubbles reach the outlet device 64 and pressure is built up thereon from the air being delivered under pressure to container 10, the bubbles are forced through the device 64, the adapter 66, into the sock 70 and from the sock 70 by being squeezed through the pores thereof into the delivery hose 68. In this sequence the bubbles are contracted and reformed and under pressure provided on the bubbles in the foam content of the container 10. The bubbles of the foam as squeezed through the sock 70 have a form that their liquid content has been minimalized but they remain sufficiently wet to be adherent and the active chemical embodied therein is substantially fully exposed at the surface of the bubbles.

The foam composition is such that it will not readily be blown away or dissipated and it tends to form an adherent blanket on the surface on which it is deposited. It is not so wet as to run off plant leaves (where fertilizer or weed killer is incorporated), the result of which may be a failure of its objective.

The foam so produced, where it merely embodies a detergent as a cleansing agent or includes a fire fighting chemical will have maximum blanketing power and incorporate a minimum of water which might soak materials in a cleansing process or provide extra sources of oxygen in a fire fighting application.

If desired and necessary for a particular application, the delivery hose may be comprised of several sections connected by adapters mounting socks 70 at longitudinally spaced locations in the delivery hose. This will provide the effect of successive wringing out of the bubbles in the foam moved through and from the hose.

In the alternative to incorporating the active chemical such as a fertilizer in the original solution in the container, it may be preferred that the original solution merely be a detergent solution to provide a basic foam, by means and in a manner above described, to the surface of which may be applied the fertilizer in the course of passage of the extremely dry bubbles of the foam through the discharge end of the delivery hose 68. Thus, referring to FIG. 4 of the drawings, in this embodiment of the invention jet nozzles 72 are introduced to position their discharge ends in the delivery hose 68, following the last sock 70 therein, for example, and angled and arranged to discharge fertilizer into the foam in the sense of its flow. In such case the fertilizer would be at the required concentration and delivered in a liquid mist like spray to spread over and entrench in the surfaces of the bubbles of the foam. The foam as discharged would not only provide an adherent blanket on the surface of deposit but its bubbles surface would expose the fertilizer (or any other chemical applied) for optimal contact to serve its desired purpose.

The invention apparatus thus described embodies the concept of uniquely providing for a staged wringing or drying of the bubbles of a simply and effectively produced foam wherein the foam can readily serve a multitude of purposes. As provided, it can selectively be employed to originally embody or later entrain active chemicals, as a vehicle for applying such chemicals in a relatively dry blanket form and with optimal results.

While the invention has been described in limited context its considerable range of use and application should be self-evident and to encompass those structures and systems comprehended by the following claims.

From the above description it will be apparent that there is thus provided a device of the character described possessing the particular features of advantage before enumerated as desirable, but which obviously is susceptible of modification in its form, proportions, detail construction and arrangement of parts without departing from the principle involved or sacrificing any of its advantages.

While in order to comply with the statute the invention has been described in language more or less specific as to structural features, it is to be understood that the invention is not limited to the specific features shown, but that the means and construction herein disclosed comprise but one of several modes of putting the invention into effect and the invention is therefore claimed in any of its forms or modifications within the legitimate and valid scope of the appended claims.

The embodiments of the invention in which an exclusive property or privilege is claimed are defined as follows:

1. Foam producing apparatus comprising, a container having inlet means providing that it receives interiorly thereof, in its bottom, a limited amount of a liquid solution having foaming properties when subjected to an introduction of air, means for injecting air into said liquid at the bottom of said container to cause portions thereof to re-form as bubbles and to rise above the level of said liquid as a layered foam-like substance, multi-apertured structure disposed within and in elevated spaced relation to the bottom of said container through the apertures of which the foam-like substance is forced to squeeze the bubbles of which it is comprised, thereby to extract liquid from the walls thereof, and tubular guide means connected with and dependent from a central area of said multi-apertured structure arranged to extend substantially to the bottom of the container for directing said extracted liquid in a guided flow, back to the bottom of said container.

2. Foam producing apparatus as in claim 1 wherein said multi-apertured structure includes a series of multi-apertured devices which are relatively spaced in superposed fashion and formed to produce a successive staged squeezing of the bubbles in the foam which rises in said container to produce a staged extraction of liquid from said bubbles characterized in that at least one of said multi-apertured devices has a funnel shape and includes a dependent tube-like structure providing said tubular guide means for producing said guided flow of extracted liquid back to the bottom of said container.

3. Foam producing apparatus as in claim 1 wherein said container is connected with a source of supply of said solution and means are provided for maintaining the level of the solution in the bottom of said container, as required.

4. Foam producing apparatus as in claim 1 wherein foam discharge means in connection with said container embody means for injecting and applying chemicals to said foam in the course of flow thereof to the intended place of its deposit.

5. Foam producing apparatus comprising, a container having inlet means providing that it receives interiorly thereof, in its bottom, a limited amount of a liquid solution having foaming properties when subjected to an introduction of air, means for injecting air into said liquid at the bottom of said container to cause portions thereof to re-form as bubbles which rise above the level of said liquid as a layered foam-like substance, a multi-apertured structure disposed within and in elevated spaced relation to the bottom of said container, through the apertures of which the foam-like substance is forced to squeeze the bubbles and thereby extract liquid from the walls thereof, said structure having a centrally positioned dependent portion reaching at least to the level of the liquid in the bottom of said container and forming surface portions along which extracted liquid may flow to the bottom of said container.

6. Foam producing apparatus as in claim 5 characterized in that means define an outlet from said container above and in spaced relation to said multi-apertured structure to discharge bubbles of the foam-like substance produced by the extraction of liquid therefrom through the medium of passage through said multi-apertured structure and means define a flow passage for delivery of the foam-like substance moving through said outlet to a place of use incorporating therein, in the path of flow of said foam-like substance, a porous device through which the foam-like substance is moved in a pressured flow to squeeze further liquid from said substance in the course of its flow.

7. Foam producing apparatus as in claim 5 characterized by a plurality of said multi-apertured structures disposed within said container, in bridging relation thereto and in spaced relation to each other and to the bottom of said container, with the centrally dependent portions thereof nesting one within the other.

8. Foam producing apparatus as in claim 7 wherein said multi-apertured structures within said container each have a bowl-like form the mouth of which is uppermost in said container and the apex portion of which forms said centrally dependent portion.

9. Foam producing apparatus comprising, a container having inlet means providing that it receives in its bottom a limited amount of a liquid solution having foaming properties when subjected to an introduction of air, means for injecting air into said liquid at the bottom of said container to cause portions thereof to re-form as bubbles and to rise above the level of said liquid as a layered foam-like substance, and liquid extraction means in said container in the path of rising layers of foam, including a plurality of funnel shaped structures the bowl portions of which are apertured and have apertures at their centers rimmed by dependent tubes providing surface portions for gravity drain of extracted liquid to the bottom of said container.

10. Foam producing apparatus as in claim 9 wherein a tube for delivering a metered flow of air under pressure to the bottom of said container is positioned in generally concentric relation to said dependent tubes to discharge centrally of said container.

11. Foam producing apparatus comprising, a container having inlet means providing that it receives, interiorly thereof, in its bottom, a limited amount of liquid solution having foaming properties when subjected to an introduction of air, means for injecting air into said liquid at the bottom of said container to cause portions thereof to re-form as bubbles and to rise above the level of said liquid as a layered foam-like substance, means in connection with said container disposed in the path of the rising layers of foam and operative thereon to extract portions of the liquid content of said bubbles which make up said foam whereby to "dry" the foam-like substance formed thereby, said extracting means including, in connection therewith, means defining surface portions thereof along which liquid may be guided, under the influence of gravity, to replenish the liquid in the bottom of the container, and said container having in connection therewith means defining an outlet to which is connected a delivery tube having in connection therewith means for injecting in and applying chemicals to said foam-like substance in the course of flow thereof through said delivery tube and said injecting means incorporating jet delivery means for said chemicals the discharge end of which is directed in the sense of the flow of said foam through and from said delivery tube to its intended place of deposit.

12. Foam producing apparatus, including an upstanding container receiving in its lower interior a foamable solution, means for releasing compressed air into said solution to create a rising foam in said container, means providing an outlet for said foam from the upper interior of said container, and an intermediately positioning funnel-shaped device in said container including a bowl portion having its mouth uppermost and bridging side walls of said container, said bowl portion of said device having numerous small apertures through which the foam is constrained to pass and in the process to have liquid squeezed therefrom, a central tube portion of said device depending from said bowl portion and reaching into the bottom interior of said container, unapertured walls of said bowl portion and said central tube portion providing continuing surfaces for extracted liquid to drain back into the foamable solution substantially in by-passing relation to rising foam.

13. A foam producing apparatus according to claim 12, characterized by another funnel-shaped device constructed like the first said device and orienting similarly to the first said device in an overhead or following relation thereto in the sense of movement of the rising foam, the central tube on said other device reaching the bottom interior of the container through the central tube of the first said device, said central tubes being in a concentric spaced relation.

14. A foam producing apparatus according to claim 13, characterized by a foam delivery hose attached to said container at said outlet, and at least one porous sock-like device in said hose through which the foam is constrained to pass before discharging from said hose.

* * * * *